United States Patent
Benoit et al.

(10) Patent No.: US 7,279,144 B2
(45) Date of Patent: Oct. 9, 2007

(54) REFLECTIVE LAMP TO MAXIMIZE LIGHT DELIVERY TO A PHOTOACTIVE CATALYST

(75) Inventors: Jeffrey T. Benoit, Willington, CT (US); Stephen O. Hay, South Windsor, CT (US); Timothy N. Obee, South Windsor, CT (US)

(73) Assignee: Carrier Corporation, Syracuse, NY (US)

( * ) Notice: Subject to any disclaimer, the term of this patent is extended or adjusted under 35 U.S.C. 154(b) by 696 days.

(21) Appl. No.: 10/668,523

(22) Filed: Sep. 23, 2003

(65) Prior Publication Data

US 2005/0061656 A1    Mar. 24, 2005

(51) Int. Cl.
B01J 19/08 (2006.01)

(52) U.S. Cl. .................. 422/186.3; 422/121

(58) Field of Classification Search .......... 422/186.3, 422/121
See application file for complete search history.

(56) References Cited

U.S. PATENT DOCUMENTS

| | | | |
|---|---|---|---|
| 4,088,802 A | | 5/1978 | Shriver, Jr. |
| 5,078,971 A | | 1/1992 | Matuda et al. |
| 5,723,947 A | * | 3/1998 | Popov et al. ............... 313/634 |
| 6,730,265 B2 | * | 5/2004 | Horton, III ................. 422/24 |

FOREIGN PATENT DOCUMENTS

| | | |
|---|---|---|
| EP | 0 975 377 | 2/2000 |
| FR | 2 838 380 | 10/2003 |
| GB | 291 754 | 9/1928 |
| JP | 59 159129 | 9/1984 |
| JP | 01 043966 | 2/1989 |
| JP | 9-299937 A * | 11/1997 |
| JP | 10 033653 | 2/1998 |
| JP | 10-281484 A * | 10/1998 |
| JP | 10 281484 | 1/1999 |
| JP | 11 033091 | 2/1999 |
| JP | 2001-9016 A * | 1/2001 |
| JP | 2001 170146 | 6/2001 |
| JP | 2001 340441 | 12/2001 |
| WO | WO97/09073 | 3/1997 |

OTHER PUBLICATIONS

International Search Report, Dec. 6, 2004.

* cited by examiner

*Primary Examiner*—Kishor Mayekar
(74) *Attorney, Agent, or Firm*—Carlson, Gaskey & Olds

(57) ABSTRACT

A lamp including a reflective portion is utilized in a fluid purification system to maximize the light delivery to a photocatalytic coating that oxidizes gaseous contaminants that adsorb onto the surface to form carbon dioxide, water, and other substances. An ultraviolet light source positioned proximate to the honeycomb activates the titanium dioxide coating. In one example, the reflective portion is a reflective coating. Light directed out of the non-reflective portion of the lamp travels towards the honeycomb and absorbs onto the photocatalytic coating. Light directed towards the reflective portion on the lamp is reflected off the surface of the reflective portion and passes through the non-reflective portion of the lamp to also absorb onto the photocatalytic coating. The reflective portion reflects light towards the honeycomb that would otherwise be misdirected away from the honeycomb, increasing efficiency of the fluid purification system.

30 Claims, 2 Drawing Sheets

REFLECTIVE LAMP TO MAXIMIZE LIGHT DELIVERY TO A PHOTOACTIVE CATALYST

BACKGROUND OF THE INVENTION

The present invention relates generally to a reflective lamp utilized in a fluid purification system that maximizes the light delivery to a photocatalytic coating that oxidizes gaseous contaminants that adsorb onto the surface to form carbon dioxide, water, and other substances.

Indoor air can include trace amounts of contaminants, including carbon monoxide and volatile organic compounds such as formaldehyde, toluene, propanal, butene, and acetaldehyde. Absorbent air filters, such as activated carbon, have been employed to remove these contaminants from the air. As air flows through the filter, the filter blocks the passage of the contaminants, allowing contaminant free air to flow from the filter. A drawback to employing filters is that they simply block the passage of contaminants and do not destroy them.

Air purification systems commonly include one lamp or one bank of lamps and one photocatalytic monolith, such as a honeycomb. A photocatalytic coating, such as titanium dioxide, is on the monolith. Titanium dioxide has been employed as a photocatalyst in a fluid purifier to destroy contaminants. When the titanium dioxide is illuminated with ultraviolet light, photons are absorbed by the titanium dioxide, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When a contaminant adsorbs onto the titanium dioxide photocatalyst, the hydroxyl radicals attack and oxidize the contaminants to water, carbon dioxide, and other substances.

If only one monolith and one lamp or one bank of lamps are employed in the air purification system, much of the light from the lamp is misdirected and does not absorb onto the photocatalytic coating. Some of this misdirected light is reflected off a reflective surface applied on the housing of the air purification system and absorbed onto the photocatalytic coating. However, much of the light is still misdirected and not used for photocatalytic purposes. Therefore, the photocatalytic efficiency for the air purification system is less than optimum.

A second monolith can be positioned on the side of the lamp opposite to the first monolith to absorb the misdirected light. However, adding a second monolith is costly and light is still misdirected from the lamp and not used for photocatalytic purposes. Reflectors can be added adjacent to the lamp or bank of lamps to direct more of the light to the monolith, but this method adds an undesirable pressure drop to the system.

Hence, there is a need for a reflective lamp utilized in a fluid purification system that maximizes the light delivery to a photocatalytic coating.

SUMMARY OF THE INVENTION

A reflective lamp utilized in a fluid purification system maximizes the light delivery to a photocatalytic coating that oxidizes gaseous contaminants that adsorb onto the surface to form carbon dioxide, water, and other substances.

A fan draws a fluid, such as air, into a fluid purification system. The fluid flows through an open passage or channel of a honeycomb. The surface of the honeycomb is reflective with a titanium dioxide photocatalytic coating. An ultraviolet light source positioned proximate to the honeycomb activates the titanium dioxide coating. The walls of the fluid purification system are preferably lined with a reflective material to reflect the ultraviolet light onto the interior surface of the open passages of the honeycomb.

The lamp includes a reflective surface. Preferably, the reflective surface is a reflective coating. Preferably, the reflective surface is on at least half of the cross-sectional area of the lamp. The reflective surface can be on either the inner surface or the outer surface of the lamp.

Light directed out of the non-reflective portion of the lamp travels towards the honeycomb and absorbs onto the photocatalytic coating. Light directed towards the reflective surface on the lamp is reflected off the surface of the reflective surface and passes through the non-reflective portion of the lamp to absorb onto the photocatalytic coating on the substrate. The reflective surface reflects light towards the honeycomb that would otherwise be misdirected away from the honeycomb, increasing photocatalytic efficiency.

When photons of the ultraviolet light are absorbed by the titanium dioxide coating, reactive hydroxyl radicals are formed. When a contaminant, such as a volatile organic compound, is adsorbed onto the titanium dioxide coating, the hydroxyl radical attacks the contaminant, abstracting a hydrogen atom from the contaminant and oxidizing the volatile organic compounds to water, carbon dioxide, and other substances.

These and other features of the present invention will be best understood from the following specification and drawings.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
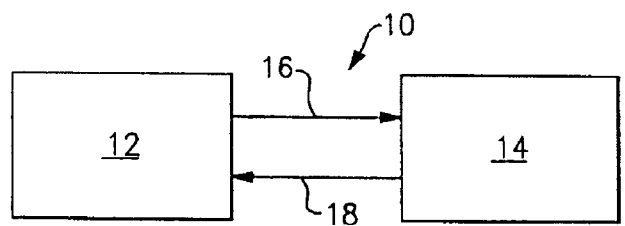
FIG. 1 schematically illustrates an enclosed environment, such as a building, vehicle or other structure, including an interior space and an HVAC system.

FIG. 1 schematically illustrates a building, vehicle, or other structure 10 including an interior space 12, such as a room, an office or a vehicle cabin, such as a car, train, bus or aircraft. An HVAC system 14 heats or cools the interior space 12. Fluid in the interior space 12, such as air, is drawn by a path 16 into the HVAC system 14. The HVAC system 14 changes the temperature of the fluid drawn 16 from the interior space 12. If the HVAC system 14 is operating in a cooling mode, the fluid is cooled. Alternately, if the HVAC system 14 is operating in a heating mode, the fluid is heated. The fluid is then returned back by a path 18 to the interior space 12, changing the temperature of the fluid in the interior space 12.

Figure 2:
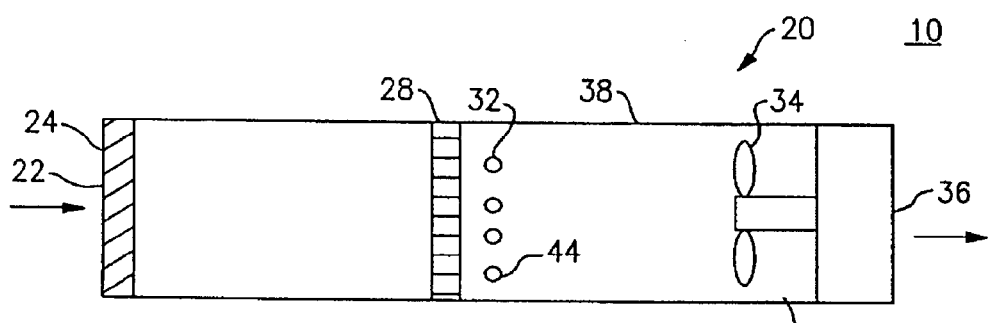
FIG. 2 schematically illustrates the fluid purification system of the present invention.

FIG. 2 schematically illustrates a fluid purification system 20 employed to purify the fluid in the building or vehicle 10 by oxidizing contaminants, such as volatile organic compounds and semi-volatile organic compounds, to water, carbon dioxide, and other substances. Volatile organic compounds are organic compounds that have a boiling point at 1 atmosphere of pressure of less than 200° C. The volatile organic compounds can be formaldehyde, toluene, propanal, butene, acetaldehyde, aldehydes, ketones, alcohols, aromatics, alkenes, or alkanes. Semi-volatile organic compounds are organic compounds having a boiling point at 1 atmosphere of pressure of greater than 200° C. The semi-volatile organic compounds can be naphthalene, PCB's, PAH's and insecticides. The fluid purification system 20 can purify the fluid before it is drawn along path 16 into the HVAC system 14 or it can purify fluid leaving the HVAC system 14 before it is blown along path 18 into the interior space 12 of the building or vehicle 10. The fluid purification system 20 can also be a stand alone unit that is not employed with a HVAC system 14.

Figure 3:
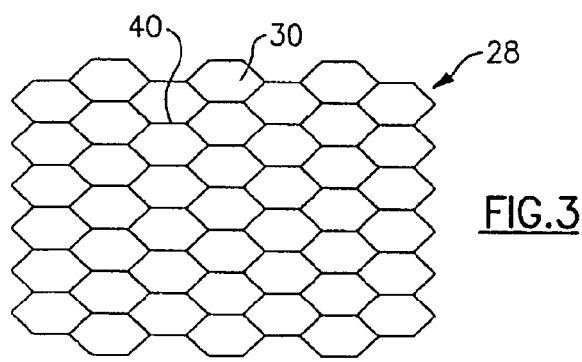
FIG. 3 schematically illustrates the honeycomb of the fluid purification system.

A fan 34 draws fluid into the fluid purification system 20 through an inlet 22. The fluid flows through a particle filter 24 that filters out dust or any other large particles by blocking the flow of these particles. The fluid then flows through a monolith or substrate 28, such as a honeycomb. In one example, the honeycomb 28 is made of aluminum or an aluminum alloy. The substrate 28 is porous and allows fluid to flow through the substrate 28. FIG. 3 schematically illustrates a front view of the honeycomb 28 having a plurality of hexagonal open passages or channels 30. The surfaces of the plurality of open passages 30 are reflective with a photocatalytic coating 40. When activated by ultraviolet light, the coating 40 oxidizes volatile organic compounds that adsorb onto the titanium dioxide coating 40. As explained below, as fluid flows through the open passages 30 of the honeycomb 28, contaminants that are adsorbed on the surface of the titanium dioxide coating 40 are oxidized into carbon dioxide, water and other substances.

A light source 32 positioned proximate to the honeycomb 28 activates the titanium dioxide photocatalytic coating 40 on the surface of the open passages 30. Preferably, the light source 32 is an ultraviolet light source which generates light having a wavelength in the range of 180 nanometers to 400 nanometers. The light source 32 has a peak wavelength at 254 nm. The light source 32 can be a mercury vapor lamp, an excimer lamp, an electrodeless lamp, an inductively coupled lamp, a radio frequency powered lamp, or a light emitting diode.

The light source 32 is illuminated to activate the titanium dioxide coating 40 on the surface of the honeycomb 28. When the photons of the ultraviolet light are absorbed by the titanium dioxide coating 40, an electron is promoted from the valence band to the conduction band, producing a hole in the valence band. The titanium dioxide coating 40 must be in the presence of oxygen and water to oxidize the contaminants into carbon dioxide, water, and other substances. The electrons that are promoted to the conduction band are captured by the oxygen. The holes in the valence band react with water molecules adsorbed on the titanium dioxide coating 40 to form reactive hydroxyl radicals.

When a contaminant is adsorbed onto the coating 40, the hydroxyl radical attacks the contaminant, abstracting a hydrogen atom from the contaminant. In this method, the hydroxyl radical oxidizes the contaminants and produces water, carbon dioxide, and other substances.

After passing through the honeycombs 28, the purified fluid then exits the fluid purifier through an outlet 36. The walls 38 of the fluid purification system 20 are preferably lined with a reflective material 42. The reflective material 42 reflects the ultraviolet light onto the surface of the open passages 30 of the honeycomb 28.

Figure 4:
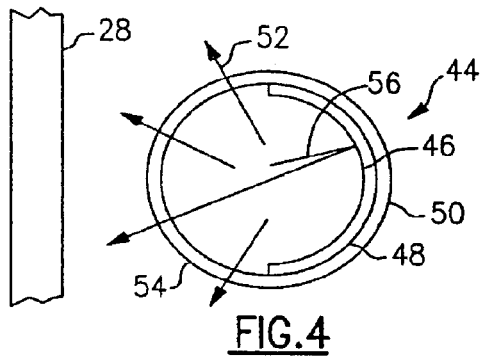
FIG. 4 schematically illustrates a lamp having a reflective surface on an inner surface of the lamp.
Figure 5:
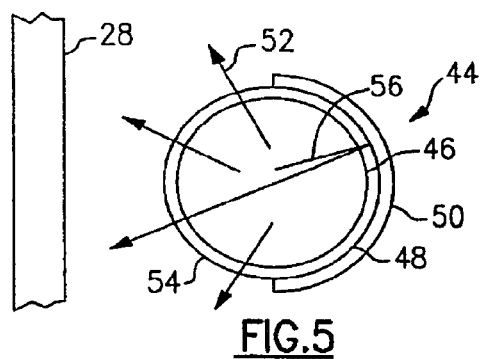
FIG. 5 schematically illustrates a lamp having a reflective surface on an outer surface of the lamp.

FIG. 4 schematically illustrates a cross-sectional view of one lamp 44 of the light source 32. The light includes a reflective surface 46 on a portion of the lamp 44. Preferably, the reflective surface 46 is on at least half of the lamp 44. The reflective surface 46 can be on the inner surface 48 of the lamp 44 as shown in FIG. 4 or the outer surface 50 of the lamp 44 as shown in FIG. 5.

Light 52 directed out of the non-reflective portion 54 of the lamp 44 travels towards the honeycomb 28 and absorbs onto the photocatalytic coating 40. Light 56 directed towards the reflective surface 46 on the lamp 44 is reflected off the surface of the reflective surface 46 and passes through the non-reflective portion 54 of the lamp 44 to absorb onto the photocatalytic coating 40 on the honeycomb 28. This light 56 is directed to the honeycomb 28, rather than being directed away from the honeycomb 28, increasing the amount of light that absorbs on the photocatalytic coating 40.

If there was no reflective surface 46, the light 56 would be directed away from the honeycomb 32 and would not be absorbed by the photocatalytic coating 40, decreasing the efficiency of the fluid purification system 20. By employing a reflective surface 46, light 56 that is originally directed away from the honeycomb 28 is directed back to the honeycomb 28 for absorption.

Preferably, at least half of the lamp 44 is reflective with the reflective surface 46. If half of the lamp 44 is reflective with the reflective surface 46, half the lamp 44 reflects light and prevents light from leaving the lamp 44 in non-preferred directions. The other half the lamp 44 includes the non-reflective portion 54 that allows light to travel from the lamp 44 and be directed to the honeycomb 28.

Preferably, the lamp 44 is cylindrical, and the reflective surface 46 is on the half of lamp 44 that is the furthest away from the honeycomb 28. Although a lamp 44 having a cylindrical cross section is illustrated and described, it is to be understood that the lamp 44 can have any shape or size. The shape of the lamp 44 and the shape of the reflective surface 46 can be designed to maximize the amount of light delivered to the photocatalytic coating 40 on the honeycomb 28.

Figure 6:
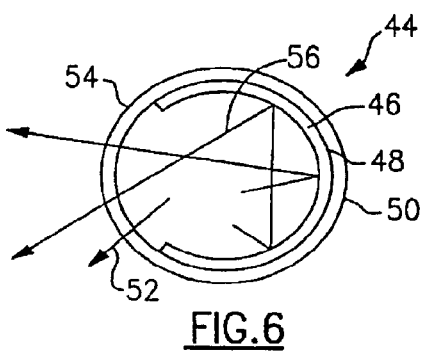
FIG. 6 schematically illustrates a lamp having a reflective surface on more than one half of the surface of the lamp.

Alternatively, as shown in FIG. 6, more than half of the lamp 44 can be reflective with the reflective surface 46 to more specifically direct the light to the honeycomb 28. If more than half of the lamp 44 is reflective with the reflective surface 48, less than half the lamp 44 includes an non-reflective portion 54. The area of the non-reflective portion 54 is smaller, allowing the light to be more accurately directed to the honeycomb 28.

By employing a reflective surface 46 on the lamp 44, more light is directed towards the honeycomb 28, increasing the efficiency of the fluid purification system 20. Therefore, the fluid purification system 20 can be made smaller, providing a cost savings. Additionally, the size, power, and quantity of the lamps 44 can be reduced, also providing a cost savings.

Figure 7:
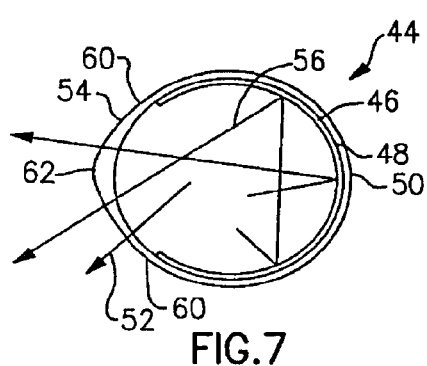
FIG. 7 schematically illustrates a lamp having a concave non-reflective surface.

Alternately, the non-reflective portion 54 of the lamp 44 is shaped to provide lensing or refraction that directs the light 56 towards the honeycomb 28. In one example, as shown in FIG. 7, the non-reflective portion 54 is a converging lens. That is, the non-reflective portion 54 of the lamp 44 includes a thinner portion 60 closer to the reflective surface 46 and a thicker potion 62 at a central point. By employing this shape, the lamp 44 can provide additional lensing or refraction to direct the light 56 to the honeycomb 28.

Additionally, the position and the distance of the honeycomb 28 relative to the lamp 44 can be adjusted to provide optimal light direction to the honeycomb 28.

In addition to directing light to the honeycomb 28, the lamp 44 can also be employed to direct light away from an undesired location. For example, the undesired location can be material that would be damaged by the light from the lamp 44, people who can be harmed by the light 44 (such as eye or skin damage), or animals or other biological organisms that can be harmed by the light.

Titanium dioxide is an effective photocatalyst to oxide volatile organic compounds to carbon dioxide, water and other substances. When a contaminant is adsorbed onto the titanium dioxide coating 40, the hydroxyl radical attacks the contaminant, abstracting a hydrogen atom from the contaminant. The hydroxyl radical oxidizes the contaminants and produces water, carbon dioxide, and other substances.

Preferably, the photocatalyst is titanium dioxide. In one example, the titanium dioxide is Millennium titania, Degussa P-25, or an equivalent titanium dioxide. However, it is to be understood that other photocatalytic materials or a combination of titanium dioxide with other metal oxides can be employed, as long as they are active supports for thermo-catalytic function. For example, the photocatalytic materials can be $Fe_2O_3$, $ZnO$, $V_2O_5$, $SnO_2$, or $FeTiO_3$. Additionally, other metal oxides can be mixed with titanium dioxide, such as $Fe_2O_3$, $ZnO$, $V_2O_5$, $SnO_2$, $CuO$, $MnO_x$, $WO_3$, $Co_3O_4$, $CeO_2$, $ZrO_2$, $SiO_2$, $Al_2O_3$, $Cr_2O_3$, or $NiO$.

The titanium dioxide can also be loaded with a metal oxide. In one example, the metal oxide is $WO_3$, $ZnO$, $CdS$, $SrTiO_3$, $Fe_2O_3$, $V_2O_5$, $SnO_2$, $FeTiO_3$, $PbO$, $CO_3O4$, $NiO$, $CeO_2$, $CuO$, $SiO_2$, $Al_2O_3$, $Mn_xO_2$, $Cr_2O_3$, or $ZrO_2$.

Although a single honeycomb 28 has been illustrated and described, it is to be understood that multiple honeycombs 28 can be employed. Additionally, although a honeycomb 28 has been illustrated and described, it is to be understood that the titanium dioxide coating 40 can be applied on any structure. The voids in a honeycomb 28 are typically hexagonal in shape, but it is to be understood that other void shapes can be employed. As contaminants adsorb onto the titanium dioxide coating 40 of the structure in the presence of a light source, the contaminants are oxidized into water, carbon dioxide and other substances.

Figure 8:
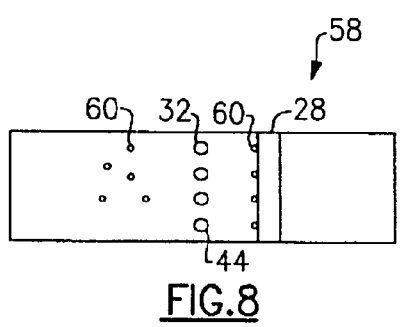
FIG. 8 schematically illustrates a lamp used in a germicidal system or a system to increase chemical reaction rates.

Alternately, as shown in FIG. 8, the lamp 44 is employed in a germidical system 64 and directs light towards an undesired biological entity 66. The biological entity can be bacterial, fungi, mold and viruses. In one example, the biological entity is suspended in a fluid, such as air. The fluid can move past the lamp 44 or can be stationary. In another example, the biological entity is on the substrate 28. Again, the biological entity can be suspended in a fluid, such as air. The fluid with the biological entity can move past the lamp 44 or can be stationary. The substrate 28 can be a food preparation surface, an HVAC system, a fluid filter, a medical surface or a food preparation conveyor belt.

As shown in FIG. 8, the lamp 44 can also be employed in a system 64 to direct light towards a fluid or a surface to increase chemical reactions rates for chemical reactions that are promoted by light without the presence of a catalyst. For example, the chemical reaction can cause the destruction of a material 66, such as ozone. The chemical reactions can be in a fluid, such as air. The fluid can be stationary or mobile. The chemical reaction can occur on a surface or a porous surface. For example, the surface can be for the display of information. Alternately, the surface can be for the transmission of light for information purposes. For example, the reactions can remove obscuring material from the surface.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A fluid purification system for purifying a fluid comprising:
   a substrate;
   a photocatalytic coating applied on said substrate; and
   a light source to activate said photocatalytic coating, said light source including a non-reflective portion that allows passage of light and a reflective portion that reflects said light to pass through said non-reflective portion of said light source wherein said non-reflective portion includes a thinner portion closer to the reflective portion and a thicker portion at a central point of the non-reflective portion.

2. The fluid purification system as recited in claim 1 wherein said light source is operative to activate said photocatalytic coating to oxidize contaminants within the fluid that are adsorbed onto said photocatalytic coating when activated by said light source.

3. The fluid purification system as recited in claim 1 wherein said light source is an ultraviolet light source.

4. The fluid purification system as recited in claim 3 wherein said light source is a mercury vapor lamp.

5. The fluid purification system as recited in claim 3 wherein said light source is an excimer lamp.

6. The fluid purification system as recited in claim 3 wherein said light source is an electrodeless lamp.

7. The fluid purification system as recited in claim 3 wherein said light source is an inductively coupled lamp.

8. The fluid purification system as recited in claim 3 wherein said light source is a radio frequency powered lamp.

9. The fluid purification system as recited in claim 3 wherein said light source is a light emitting diode.

10. The fluid purification system as recited in claim 3 wherein said light source generates said light having a wavelength between 180 nm and 400 nm.

11. The fluid purification system as recited in claim 10 wherein said light source has a peak wavelength of 254 nm.

12. The fluid purification system as recited in claim 1 wherein said photocatalytic coating is titanium oxide.

13. The fluid purification system as recited in claim 1 wherein photons from said light source are absorbed by said photocatalytic coating to form a reactive hydroxyl radical that oxidizes contaminants within the fluid in the presence of oxygen and water to water and carbon dioxide.

14. The fluid purification system as recited in claim 1 wherein contaminants within the fluid are a volatile organic compound including at least one of formaldehyde, toluene, propanal, butene, acetaldehyde, aldehyde, ketone, alcohol, aromatic, alkene, and alkane.

15. The fluid purification system as recited in claim 1 wherein contaminants within the fluid are a semi-volatile organic compound including at least one of naphthalene, polychlorinated biphenyl, polycyclic aromatic hydrocarbon and an insecticide.

16. The fluid purification system as recited in claim 1 wherein said reflective portion covers a portion of said light source.

17. The fluid purification system as recited in claim 16 wherein said reflective portion covers more than half of said portion of said light source.

18. The fluid purification system as recited in claim 1 wherein said non-reflective portion of said lamp is proximate to said substrate and said reflective portion of said light source is distal to said substrate.

19. The fluid purification system as recited in claim 1 wherein said substrate is an array of voids separated by a solid.

20. The fluid purification system as recited in claim 1 further including a housing, the fluid purification system is in said housing, and walls of said housing are lined with a reflective material.

21. The fluid purification system as recited in claim 1 wherein said light source is cylindrical.

22. The fluid purification system as recited in claim 1 wherein said reflective portion is a reflective coating.

23. The fluid purification system as recited in claim 1 wherein said non-reflective portion of said light source is shaped to direct said light to said substrate.

24. The fluid purification system as recited in claim 1 wherein said lens of said light source is a converging lens.

25. The fluid purification system as recited in claim 1 wherein the fluid is air.

26. The fluid purification system as recited in claim 1 wherein said substrate is porous and allows a fluid to flow through said substrate.

27. The fluid purification system as recited in claim 1 wherein said light source directs said light towards said substrate and directs said light away from an undesired location.

28. The fluid purification system as recited in claim 1, wherein the lens is a section of a body having a circular cross-section, wherein the non-uniform thickness of the section transitions into a uniform thickness section of the circular cross-section.

29. The fluid purification system as recited in claim 1, wherein the lens comprises a section of a cylindrical body circumscribing the fight source.

30. The fluid purification system as recited in claim 1, wherein the lens surrounds an area from which the light source emits light.

* * * * *

UNITED STATES PATENT AND TRADEMARK OFFICE
CERTIFICATE OF CORRECTION

PATENT NO. : 7,279,144 B2  Page 1 of 1
APPLICATION NO. : 10/668523
DATED : October 9, 2007
INVENTOR(S) : Benoit et al.

It is certified that error appears in the above-identified patent and that said Letters Patent is hereby corrected as shown below:

Claim 29, Column 8, line 24: "fight" should read as --light--

Signed and Sealed this

Twenty-fifth Day of December, 2007

JON W. DUDAS
*Director of the United States Patent and Trademark Office*